(12) United States Patent
Prior et al.

(10) Patent No.: US 10,302,539 B2
(45) Date of Patent: May 28, 2019

(54) COLLAPSIBLE SHELF ASSEMBLY

(71) Applicant: Archipelago Group LLC, Lakewood, CO (US)

(72) Inventors: Bruce Prior, Lakewood, CO (US); George Prior, Culver City, CA (US)

(73) Assignee: ARCHIPELAGO GROUP LLC, Lakewood, CO (US)

( * ) Notice: Subject to any disclaimer, the term of this patent is extended or adjusted under 35 U.S.C. 154(b) by 0 days.

(21) Appl. No.: 15/848,411

(22) Filed: Dec. 20, 2017

(65) Prior Publication Data

US 2018/0177337 A1 Jun. 28, 2018

Related U.S. Application Data

(60) Provisional application No. 62/438,088, filed on Dec. 22, 2016.

(51) Int. Cl.
*G01N 3/56* (2006.01)
*A47J 37/07* (2006.01)
*A47B 5/04* (2006.01)
*A47B 5/02* (2006.01)

(52) U.S. Cl.
CPC ............ *G01N 3/56* (2013.01); *A47J 37/0786* (2013.01); *A47B 5/02* (2013.01); *A47B 5/04* (2013.01); *A47J 2037/0777* (2013.01); *G01N 2203/0676* (2013.01); *G01N 2203/0694* (2013.01)

(58) Field of Classification Search
CPC ..... A47B 5/00; A47B 5/02; A47B 5/04; A47J 37/0786

USPC ....................................... 108/42, 47, 43, 152
See application file for complete search history.

(56) References Cited

U.S. PATENT DOCUMENTS

| | | | | |
|---|---|---|---|---|
| 128,739 | A * | 7/1872 | Mahan | A47B 23/002 108/43 |
| 527,108 | A * | 10/1894 | Cooper | A47B 97/08 312/231 |
| 2,768,042 | A * | 10/1956 | Persinger | A47B 1/00 108/148 |
| 2,787,995 | A * | 4/1957 | Alter | A47J 37/0763 126/25 R |
| 2,844,429 | A * | 7/1958 | Frey | A47B 23/002 108/115 |
| 2,886,386 | A * | 5/1959 | Spitzer | A47J 37/0745 108/135 |
| 4,337,751 | A | 7/1982 | Sampson et al. | |
| 4,688,541 | A * | 8/1987 | Stephen | A47J 37/0786 108/152 |

(Continued)

OTHER PUBLICATIONS

Tepro, www.tepro-gmbh.de; El Monte 1032 Kettle Grill with Side Shelf; Internet, http://www.amazon.com.uk/Tepro-El-Monte-1032-Kettle-Grill/dp/B004L6HYOE; Jan. 27, 2011, 3 pages; Amazon; UK.

*Primary Examiner* — Jose V Chen
(74) *Attorney, Agent, or Firm* — Olav M. Underdal; IDP Patent Services

(57) ABSTRACT

A collapsible shelf assembly that may be adapted to be supportably engaged by a cooking structure. The collapsible shelf assembly may comprise a first support panel and a second support panel for supporting a shelf panel, and may be stabilized by stabilizer members. The collapsible shelf assembly may be moveable between a stowed position and a deployed position.

27 Claims, 10 Drawing Sheets

(56) References Cited

U.S. PATENT DOCUMENTS

| | | | | |
|---|---|---|---|---|
| 5,127,339 A | * | 7/1992 | Hood, Jr. | A47B 23/002 108/42 |
| 5,156,096 A | * | 10/1992 | Lamprey | A47B 96/027 108/108 |
| 5,906,193 A | * | 5/1999 | Leach | A47J 37/0786 126/25 R |
| 5,947,032 A | * | 9/1999 | Meier | A47B 5/06 108/33 |
| 6,105,509 A | * | 8/2000 | Altfeder | A47B 43/00 108/134 |
| 6,142,140 A | | 11/2000 | Shumaker | |
| 6,496,360 B1 | * | 12/2002 | Cordes | A47B 23/002 108/43 |
| 6,755,188 B2 | | 6/2004 | Skidmore et al. | |
| 8,424,464 B2 | * | 4/2013 | Korpi | A47B 23/044 108/27 |
| 8,794,162 B2 | * | 8/2014 | Hisata | B64D 11/00 108/43 |
| 9,551,459 B2 | * | 1/2017 | Heyen | A47B 23/002 |
| 2006/0162623 A1 | * | 7/2006 | Ciulla | A47B 5/06 108/48 |
| 2007/0283854 A1 | * | 12/2007 | Taylor | B66F 7/28 108/42 |
| 2010/0236452 A1 | * | 9/2010 | Ruddy | A47B 23/002 108/6 |

* cited by examiner

Grill System With Collapsible Shelf Assembly

Method For Using Collapsible Shelf Assembly with a Grill

COLLAPSIBLE SHELF ASSEMBLY

CROSS-REFERENCE TO RELATED APPLICATIONS

This application claims the benefit of U.S. Provisional Application No. 62/438,088, filed Dec. 22, 2016, which is hereby included by reference in its entirety.

FIELD OF THE INVENTION

The present invention relates generally to the field of accessories for barbeque grills, and more particularly to methods and systems for providing tables or shelves as an accessory to a barbeque grill.

BACKGROUND OF THE INVENTION

Grilling foods on a cooking structure is a pastime enjoyed by people around the world. Many people use a free-standing cooking structure including a grill configured to use a heat source to grill foods. In preparation for grilling foods, foods may be prepared in a kitchen and then foods may be moved along with various grilling items, outside for grilling. Traditionally, these items are placed on a table or another similar independent support structure away from the grill.

However, tables and other independent support structures may be large and cumbersome such that they are difficult to position near the grill when grilling. In this regard, tables may fail to provide a surface sufficiently close to the grill to receive items allowing ease of access while grilling. Furthermore, while transportation of a grill may be relatively easy, transportation of a table along with the grill may be challenging due to their bulkiness.

As such, considering the foregoing, it may be appreciated that there continues to be a need for novel and improved devices and methods for grill tables.

SUMMARY OF THE INVENTION

The foregoing needs are met, to a great extent, by the present invention, wherein in aspects of this invention, enhancements are provided to the existing model of grill tables and shelves.

The present disclosure relates to a collapsible grill shelf, for example, for use in supporting foods and various other grilling items. When the collapsible grill shelf is no longer needed, the collapsible grill shelf may then be collapsed and stored in a stowed position, possibly in the interior of the cooking structure itself.

It has been recognized herein that because tables and other independent support structures may be challenging to move within proximity of a cooking structure, it may be desirable for a shelf to be engageable directly with a cooking structure. In this manner, foods and various other items may be disposed on a surface of the collapsible grill shelf for easy access before, during, and after grilling foods. Moreover, when the collapsible grill shelf is no longer in use, it may be collapsed and stored in a stowed position. The collapsible grill shelf may be ideal for grilling and yet does not require any additional space for storage or transportation of the cooking structure.

To meet the needs of the grilling challenges discussed above, the present disclosure presents an elegantly simple, yet robust design that facilitates convenient grilling. In this regard, according to one aspect a collapsible shelf assembly adapted to be supportably engaged by a grill bowl is provided. Generally, the collapsible grill shelf may include a shelf panel having a surface defined between a cantilevered edge portion and an arcuate edge portion and between opposing side edge portions. The arcuate edge portion may be conformingly shaped to an edge of the grill bowl. An attachment member may extend along at least a portion of the arcuate edge portion.

Further, the attachment member may be adapted to engage the edge of the grill bowl. A first support panel and a second support panel may each be engaged with the shelf panel on a portion of the shelf panel opposite the surface. Generally, each of the first support panel and the second support panel may be configured to be moved between a deployed position and a stowed position. The support panels extend in a direction away from the surface when in the deployed position. The support panels are disposed in a folded configuration substantially parallel to the surface when in the stowed position.

As may be appreciated, there may be a number of feature refinements for the collapsible shelf assembly. According to one feature refinement, at least one stabilizer may be engaged with each of the first support panel and the second support panel to limit travel of the plurality of support panels beyond a predetermined orientation relative to the shelf panel when in the deployed position.

According to a further related aspect, the at least one stabilizer may be engaged with each one of the first support panel and the second support panel to secure the support panels in the deployed position.

According to a further related aspect, the at least one stabilizer may comprise at least one of a rigid member extending between a respective one of the first support panel or the second support panel and the shelf panel.

According to a further related aspect, the stabilizer may comprise a cable extending between an anchor location and a given one of the first and second support panels.

According to a further related aspect, the anchor location for the cable corresponding to the first support panel may be disposed on the second support panel and the anchor location for the cable corresponding to the second support panel may be disposed on the first support panel.

According to a further related aspect, the anchor location for the cable corresponding to the first support panel may be disposed on the second support panel adjacent to the cantilevered edge and may terminate on the first support panel adjacent to the arcuate edge. The anchor location for the cable corresponding to the second support panel may be disposed on the first support panel adjacent to the cantilevered edge and may terminate on the second support panel adjacent to the arcuate edge.

According to a further related aspect, when in the deployed position, the cables extending between the first and second support panels may be tensioned by way of action of the first and second support panels on the cable.

According to a further related aspect, when in the deployed position, an included angle between the first support panel and the shelf panel and between the second support panel and the shelf panel may be obtuse.

According to a further related aspect, the first support panel may extend along substantially all of a first of the opposing side edge portions and the second support panel may extend along substantially all of a second of the opposing side edge portions.

According to a further related aspect, the first support panel may be hingedly connected to the shelf panel at the first of the opposing side edge portions and the second support panel may be hingedly connected to the shelf panel at the second of the opposing side edge portions.

According to a further related aspect, the first support panel and the second support panel may each comprise a grill bowl engagement portion that may be contactable with a portion of the grill bowl extending from the edge of the grill bowl when the attachment member is engaged to the edge of the grill bowl and the first and second support panels are in the deployed position.

According to a further related aspect, the grill bowl engagement portion may correspondingly be contoured to the portion of the grill bowl extending from the edge of the grill bowl.

According to a further related aspect, the grill bowl engagement portion may comprise a non-slip surface.

According to a further related aspect, the attachment member may further comprise at least one arcuate channel portion for receiving the edge of the grill bowl.

According to a further related aspect, the arcuate channel may extend along substantially all of the arcuate edge of the shelf panel.

According to a further related aspect, the cantilevered edge portion may comprise a plurality of accessory hooks.

In another aspect, a method can be provided for use of a collapsible shelf assembly with a grill bowl Initially, a first support panel and a second support panel may be moved from a stowed position to a deployed position. The first support panel and the second support panel may each be engaged with an opposite portion of a shelf panel. Then, the travel of the first support panel and the second support panel from the stowed position to the deployed position may be limited beyond a predetermined orientation relative to the shelf panel with at least one stabilizer engaged with each of the first support panel and the second support panel. Then, an attachment member, which extends along at least a portion of an arcuate edge portion of the shelf panel, may be engaged with an edge of the grill bowl. Once engaged, the first support panel and the second support panel may be contacted with a portion of the grill extending from the edge of the grill bowl, such that the shelf panel may be supportably engaged by the edge of the grill bowl and first support panel and the second support panel.

According to one feature refinement of the second aspect, the travel of the first support panel and the second support panel may be limited with the at least one stabilizer, such that when the shelf panel is loaded, the load is distributed between the first support panel and the second support panel at least in part through the at least one stabilizer.

According to a further related aspect, the at least one stabilizer may limit the travel of the first support panel and the second support panel by tension of a cable.

According to a further related aspect, a first stabilizer may be engaged with the first support panel and the shelf panel, and a second stabilizer may be engaged with the second support panel and the shelf panel. Further, the first and second stabilizers may be engaged such that the first support panel and the second support panel may be locked in the deployed position.

According to a further related aspect, the attachment member may be disengaged from the edge of the grill bowl. Then, the first support panel and the second support panel may be moved from the deployed position to the stowed position, wherein when in the stowed position the first support panel and the second support panel may be substantially parallel to the shelf panel.

In addition to the exemplary aspects and embodiments described above, further aspects and embodiments will become apparent by reference to the accompanying drawings forming a part of this specification wherein like reference characters designate corresponding parts in the several views.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1A:
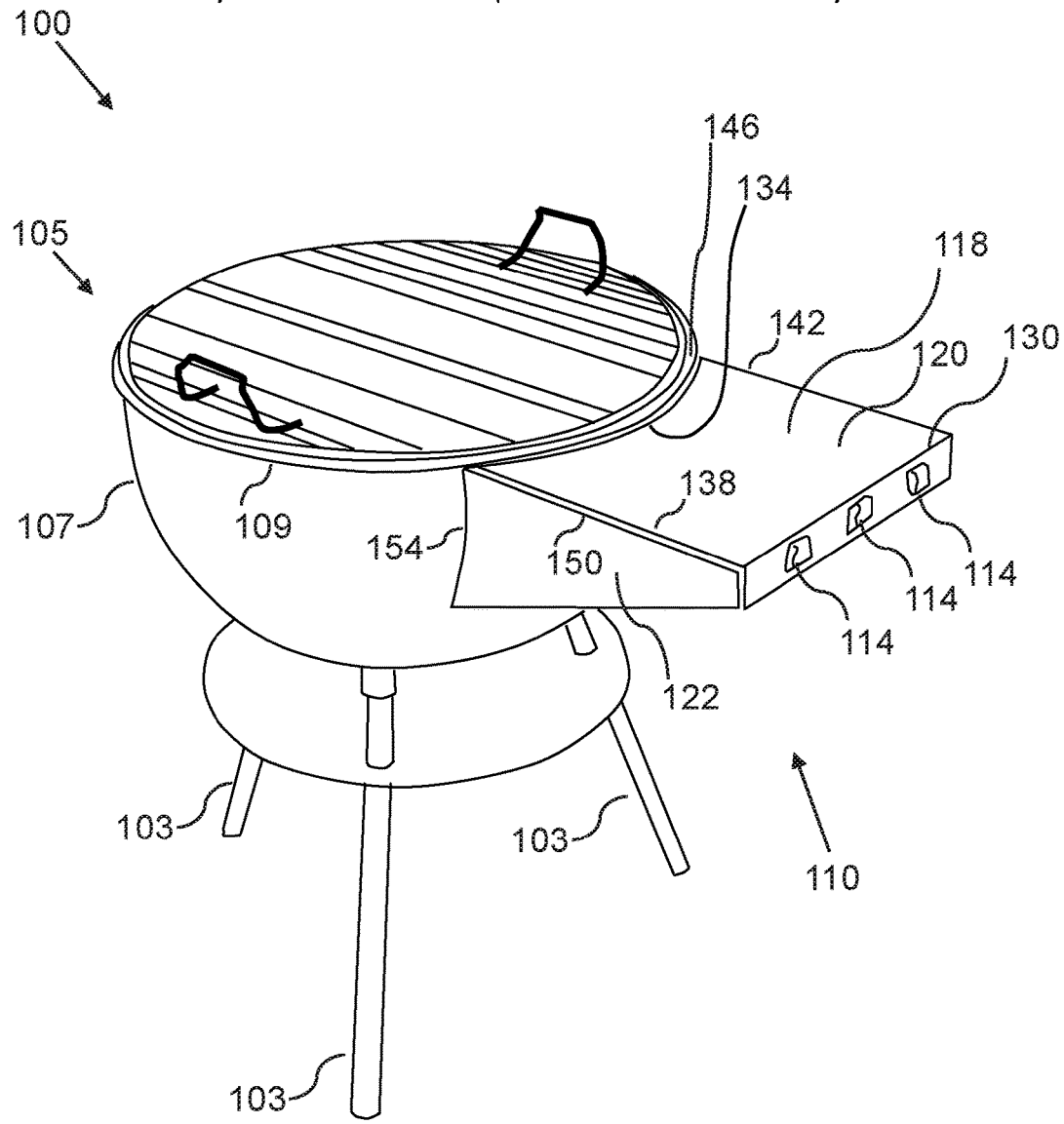
FIG. 1A is a perspective view of a collapsible shelf assembly engaged with a grill bowl, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a grill system 100 with reference to FIG. 1, in such manner that like reference numerals refer to like components throughout; a convention that we shall employ for the remainder of this specification.

In various related embodiments, disclosed herein are utilities (e.g., apparatuses, systems, processes, etc.) related to a collapsible shelf assembly. The collapsible shelf assembly may be engaged with a cooking structure (e.g., a charcoal grill) to enable a user to place items near the cooking structure. The collapsible shelf assembly may be disposed in a deployed position or a stowed position. In turn, the collapsible shelf assembly may be more conveniently stored when in the stowed position. In this regard, the collapsible shelf assembly may include a shelf panel having a surface defined between a cantilevered edge portion and an arcuate edge portion. The shelf panel may also extend between opposing side edge portions. The arcuate edge portion may include at least one attachment member that is operative to engage the cooking structure to which the collapsible shelf assembly is to be engaged. The collapsible shelf assembly may further include a first support panel and a second support panel that are each engaged with the shelf panel enabling the collapsible shelf assembly to be disposed between a deployed position and a stowed position.

Figure 1B:
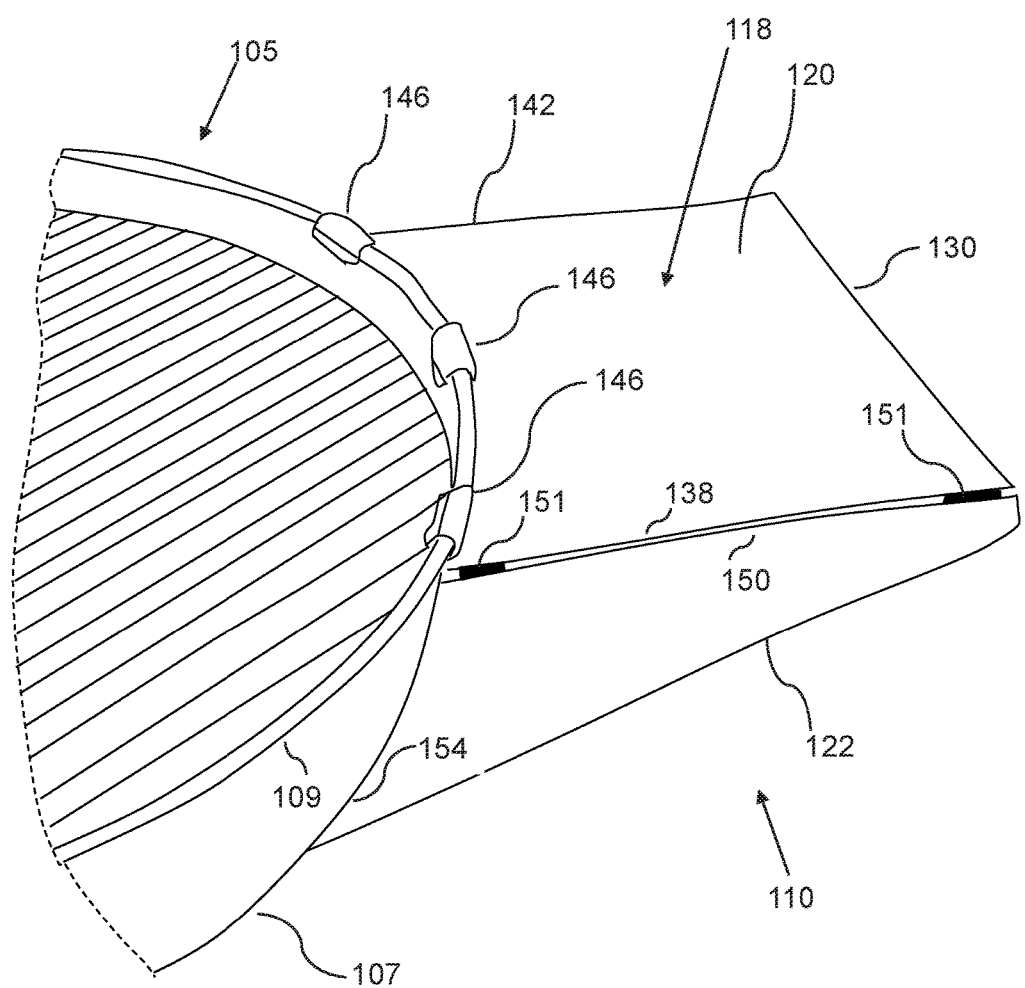
FIG. 1B is a detailed perspective view of a collapsible shelf assembly engaged with a grill bowl, according to an embodiment of the invention.

In an embodiment, FIGS. 1A and 1B show a perspective view of a grill system 100 including a collapsible shelf assembly 110 supportably engaged by a cooking structure 105. As depicted, the collapsible shelf assembly 110 may be supportably engaged by the cooking structure 105 such that a surface 120 (e.g., a top surface) of the collapsible shelf assembly 110 can be utilized to hold, store, or support any items a user may desire. For example, foods, grill tools, or other items may be placed on the surface 120 of the collapsible shelf assembly 110. As may be appreciated, the collapsible shelf assembly 110 can be supported (e.g., by a collapsible shelf assembly support structure discussed in detail below), such that heavy roasts, pans, foods, etc. may be safely placed thereon. Furthermore, the collapsible shelf assembly 110 may be collapsible such that it may be folded and stowed, for example, 110 in the cooking structure 105 when the cooking structure/grill 105 is not in use.

In related embodiments, the cooking structure 105 that the collapsible shelf assembly 110 is adapted to be supportably engaged by may be of any shape and size. As illustrated in the embodiment of FIGS. 1A and 1B, the cooking structure may include a grill bowl 107 configured to receive a heat source (e.g., charcoal briquettes) within an interior of the bowl 107. A lid (not shown) may be disposed over the bowl 107 so that the lid nests about a circumference of an edge 109 of the grill bowl 107. The cooking structure 105 may be freestanding. For instance, the cooking structure 105 may include one or more support legs 103 configured to support the weight of the cooking structure 105 and any associated components of the present invention.

Figure 2A:
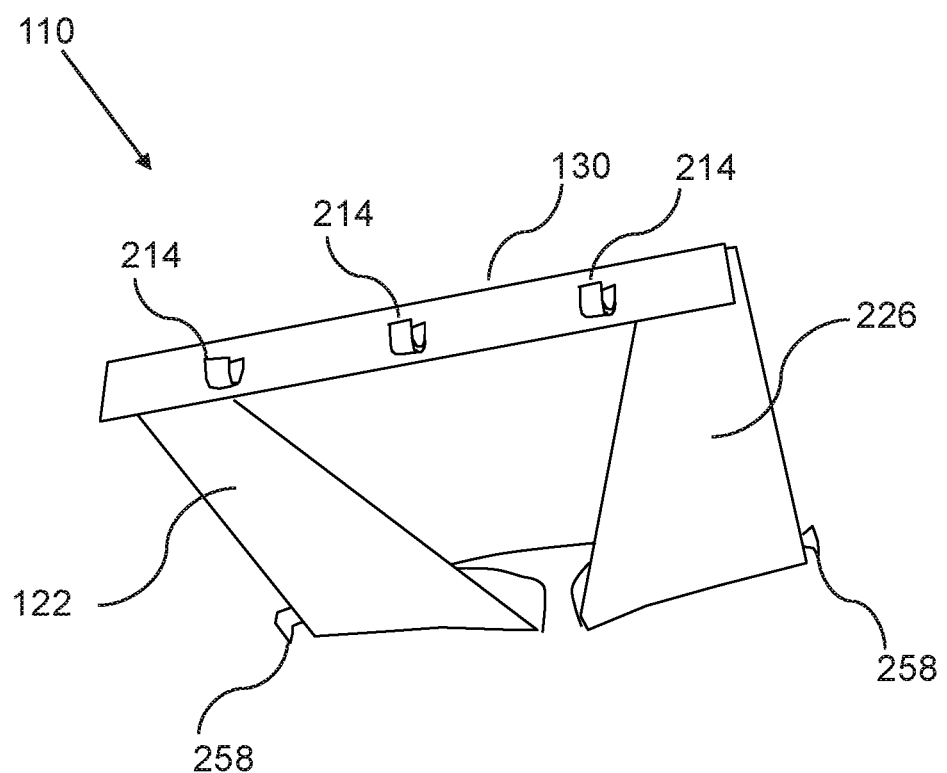
FIG. 2A is a perspective view of a collapsible shelf assembly in a stowed position, according to an embodiment of the invention.

In another related embodiment, the collapsible shelf assembly 110 can include a shelf panel 118. The collapsible shelf assembly 110 can include a first support panel 122 and a second support panel 226 (shown in FIG. 2A), collectively referred to as the support panels 122 226. The first support panel 122 and the second support panel 226 may each be configured to be movable between a stowed position and a deployed position. When the first support panel 122 and the second support panel 226 are in the deployed position, the support panels 122, 226 may extend in a direction that is at least generally directed away from the surface 120 of the shelf panel 118. As illustrated in FIG. 2A, when the support panels 122, 226 are in the stowed position, the support panels 122, 226 are disposed in a partially folded configuration. When the support panels 122, 226 are disposed in a completely folded configuration, the support panels 122, 226 may be substantially parallel to the surface 120 of the shelf panel 118

As illustrated in the embodiment of FIGS. 1A and 1B, the surface 120 of the shelf panel 118 may be defined between a cantilevered edge portion 130 and an arcuate edge portion 134 and between opposing side edge portions 138 and 142. The first support panel 122 may be engaged with the first opposing side edge portion 138 and the second support panel 226 may be engaged with the second opposing side edge portion 142. The arcuate edge portion 134 may be conformingly shaped to the edge 109 of the grill bowl 107 of the cooking structure 105. In this regard, one or more attachment members 146 may be disposed and extend along at least a portion of the arcuate edge 134 of the surface 120 of the shelf panel 118. The one or more attachment members 146 may be adapted to engage the edge 109 of the grill bowl 107. The one or more attachment members 146 can extend along the entirety of the arcuate edge 134. In other embodiments, the one or more attachment members 146 may only engage the edge 109 of the grill bowl 107 along a portion or portions of the arcuate edge 134, such as for example a middle portion of the arcuate edge 134. For example, as illustrated in FIG. 1B, three attachment members 146 may engage the edge 109 from three equally spaced portions of the arcuate edge 134 (visible in FIG. 1A). In this regard, the attachment member(s) 146 may be of any suitable shape enabling attachment to the cooking structure 105. For example, the one or more attachment members 146 can be configured with a curved/arcuate channel portion 247, as shown in FIG. 2E, such as a "U" or "V" shaped channel adapted to receive the edge 109 thereon, for example such that the "U" or "V" shaped channel hooks onto the edge 109. The arcuate channel portion 247 can also be described as a curved hook portion 247. Alternatively, the one or more attachment members 146 may instead be a "C" shaped channel adapted to receive the edge 109 thereon. Furthermore, the one or more attachment members 146 may be sized such that a lid of a cooking structure may still be accepted on the grill bowl 107 when the one or more attachment members 146 are engaged with the edge 109.

Figure 2B:
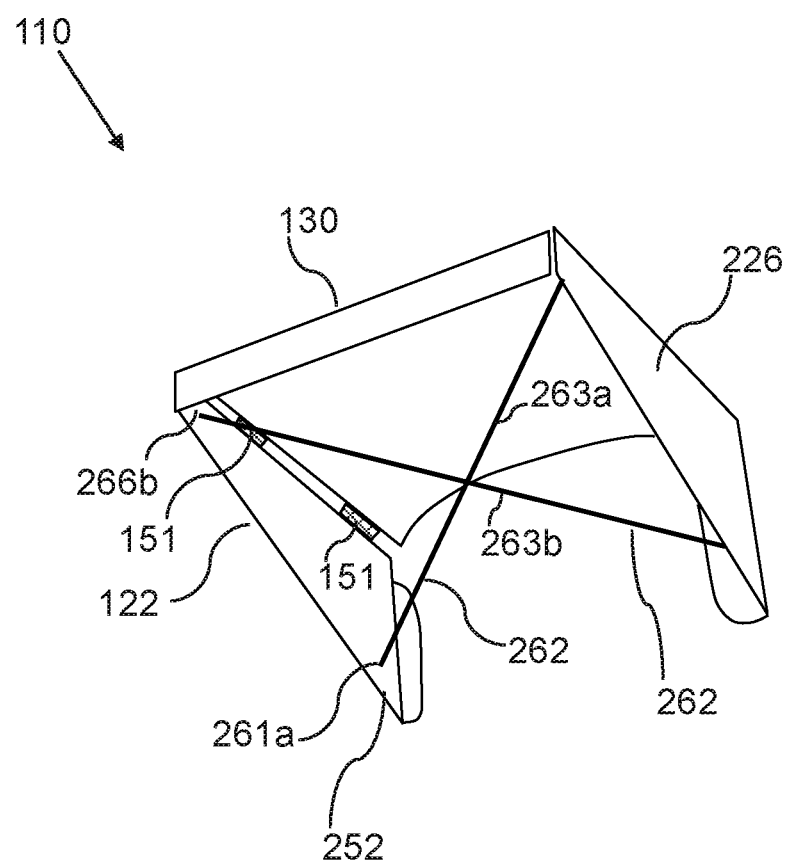
FIG. 2B is a first perspective view of the collapsible shelf assembly of FIG. 2A in a deployed position, according to an embodiment of the invention.

In yet another related embodiment, as shown in FIGS. 1B and 2B, the support structure for the shelf panel 118 can include the first support panel 122, the second support panel 226, and at least one stabilizer 262. The first support panel 122 and the second support panel 226 may be defined as each including a support side edge portion 150 and a grill bowl engagement portion 154. The support side edge portion 150 for each respective one of the first support panel 122 and the second support panel 226 may be movably connected along at least a portion of a corresponding one of the first opposing side edge portion 138 and the second opposing side edge portion 142. At least one stabilizer 262 may be used to limit travel of the support panels 122, 226 when being moved from a stowed position to a deployed position. Each of the first support panel 122, second support panel 226, the support side edge portion 150, and the stabilizer 262 will be discussed below in greater detail.

In another related embodiment, the support side edge portion 150 for each respective one of the first support panel 122 and the second support panel 226 may be movably connected with a corresponding one of the first opposing side edge portion 138 or the second opposing side edge portion 142 of the shelf panel 118 in any manner suitable to allow movement from a stowed position to a deployed position. For example, one or more hinge elements 151 may be provided to allow for the first support panel 122 to be movably connected with the first opposing side edge portion 138. One or more hinge elements 153 may be provided to allow for the second support panel 226 to be movably connected with the second opposing side edge portion 142 (as best seen in FIG. 2D). As such, the support panels 122, 226 may be hingedly connected along at least a portion of the first opposing side edge portion 138 and second opposing side edge portion 142, respectively. For example, a piano hinge may be provided and disposed along the portion of the first opposing side edge portion 138 and second opposing side edge portion 142 In one embodiment, the support side edge portion 150 of the respective support panels 122, 226 may be hingedly connected along only a portion of the corresponding first opposing side edge portion 138 and the second opposing side edge portion 142.

In a related embodiment, as shown in FIG. 1A, the support side edge portion 150 of the first support panel 122 may be hingedly connected substantially along the entirety of the first opposing side edge portion 138. The support side edge portion 150 of the second support panel 226 may be hingedly connected substantially along the entirety of the second opposing side edge portion 142. For example, a barrel hinge 151 may be provided to hingedly connect the support side edge portion 150 of the first support panel 122 to the first opposing side edge portion 138. The barrel hinge 153 may be provided to hingedly connect the support side edge portion 150 of the second support panel 226 to the second opposing side edge portion 142.

Figure 2C:
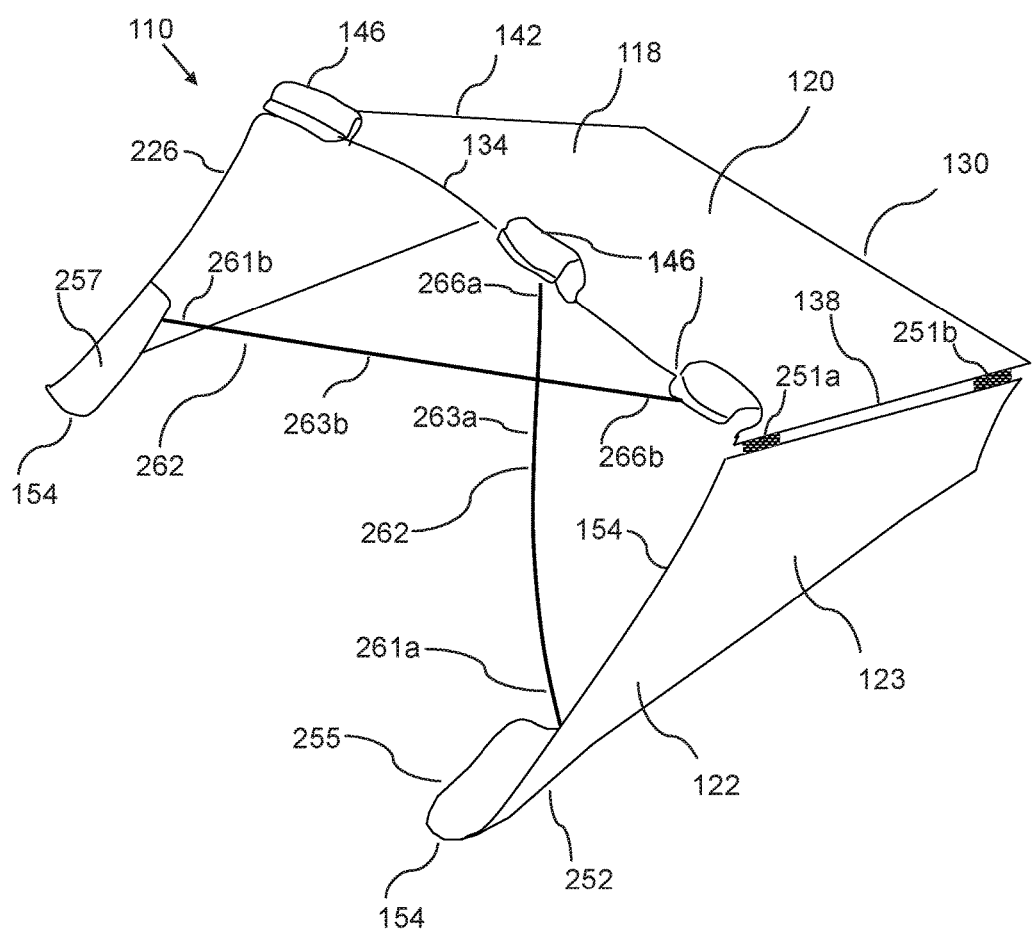
FIG. 2C is a second perspective view of the collapsible shelf assembly of FIG. 2A in a deployed position, according to an embodiment of the invention.
Figure 2D:
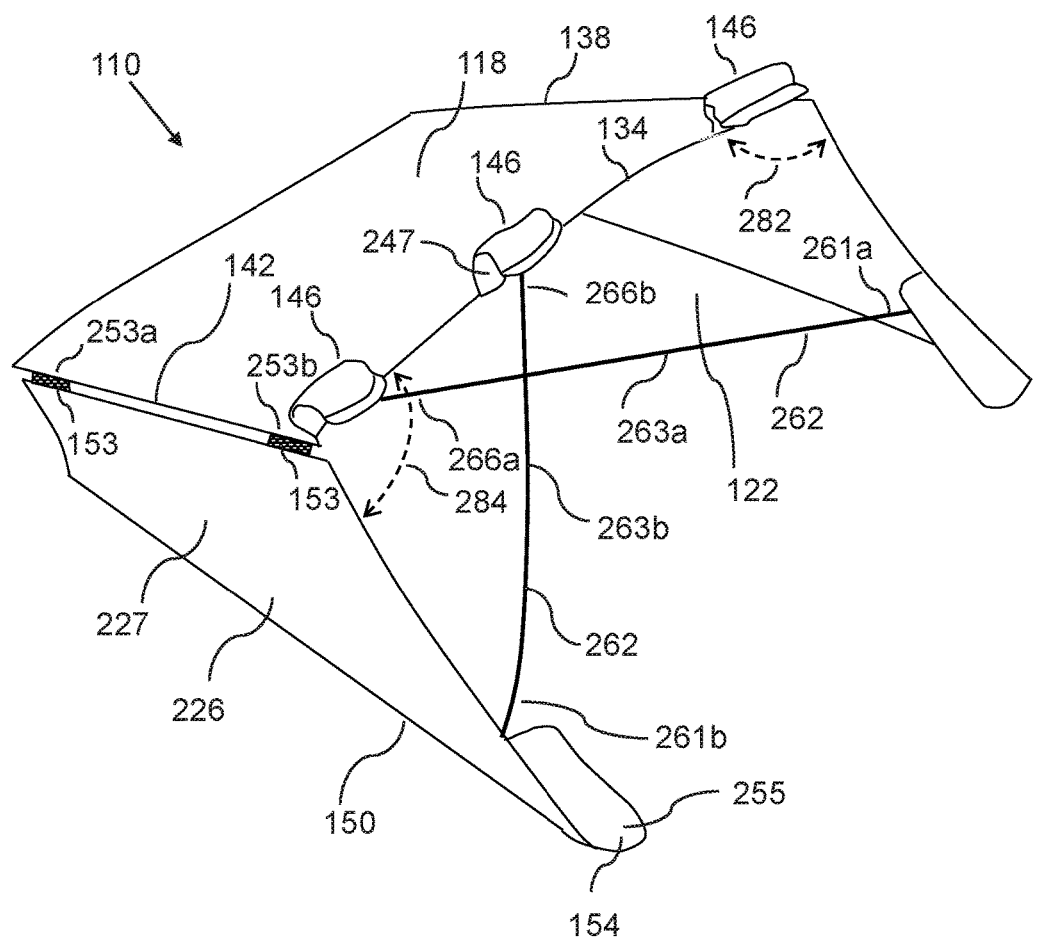
FIG. 2D is a third perspective view of the collapsible shelf assembly of FIG. 2A in a deployed position, according to an embodiment of the invention.
Figure 2E:
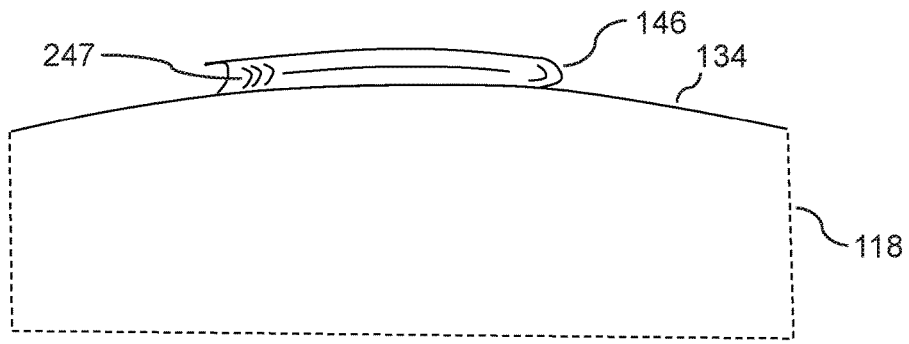
FIG. 2E is a bottom view of a front edge of the collapsible shelf assembly showing an arcuate channel portion, according to an embodiment of the invention.

In a further related embodiment, as shown in FIG. 2C, two barrel hinges 251a, 251b may be disposed at opposite ends of the support side edge portion 150 of the first support panel 122.

In a further related embodiment, as shown in FIG. 2D, two barrel hinges 253a, 253b may be disposed at opposite ends of the support side edge portion 150 of the second support panel 226.

In a related embodiment, as shown in FIGS. 1B and 2C, the first support panel 122 and the second support panel 226 may each include corresponding a grill bowl engagement portion 154. As illustrated in FIG. 1B, the grill bowl engagement portion 154 may be defined at or along an edge of the support panel 122, 226. Alternatively, as illustrated in FIGS. 2C and 2D, the grill bowl engagement portion 154 may include a tab defining a surface 255 extending in a direction that is at least generally orthogonal to a first surface 123 of the first support panel 122 or a second surface 227 of the second support panel 226.

In a related embodiment, as shown in FIG. 1B, the grill bowl engagement portion 154 may be contactable with a portion of the grill bowl 107 extending from the edge 109 when the attachment member 146 is engaged with the edge 109 and the support panels 122, 226 are in the deployed position. In this regard, the grill bowl engagement portion 154 may be contoured to the portion of the grill bowl 107 extending from the edge 109 of the grill bowl 107.

In yet a related embodiment, as shown in FIG. 2C, to further aid in supporting the shelf panel 118, the grill bowl engagement portion 154 can include a non-slip treatment 257 that engages the grill bowl 107. For example, the non-slip surface 257 can be a rubber pad disposed between the engagement portion 154 and the grill bowl 107. Alternatively, the engagement portion 154 may have a non-slip (e.g., rubber) coating. The non-slip surface 257 may also help to secure the grill bowl engagement portion 154 against the grill bowl 107 (i.e., preventing lateral movement of the support panels 122, 226 relative to the grill bowl 107 when in contact therewith).

In another related embodiment, as shown in FIG. 2A, the collapsible shelf assembly 110 can be shown in the stowed position. Even in the partially folded configuration as shown, the collapsible shelf assembly 110 takes up less space than in the deployed position. In this regard, when in the stowed position, the collapsible shelf assembly 110 may be stored in an interior of the cooking structure 105 when the cooking structure 105 is not in use. By storing the collapsible shelf assembly 110 inside the cooking structure 105 the collapsible shelf assembly 110 is not only protected from the elements (e.g., sun, rain, wind, snow, etc.), but further reduces the likelihood of the losing the collapsible shelf assembly 110 because of misplacement or theft. Storing the collapsible shelf 110 inside the cooking structure 105 further enables easy transportation of the entire system 100. From the stowed position, the first support member 122 and the second support member 226 may be moved (e.g., rotated about the hinges 151, 153) to a deployed position (e.g., to a predetermined orientation relative to the shelf panel) as illustrated in FIG. 2B. As illustrated in FIG. 2D, when the collapsible shelf assembly 110 is in the deployed position a first angle 282 between the first support panel 122 and the shelf panel 118, and a second angle 284 between the second support panel 226 and the shelf panel 118 may be obtuse. In this regard, at least one stabilizer 262 can be used to limit travel of the support panels 122, 226 within a predetermined range of acceptable angles for the first angle 282 and the second angle 284, which for example can be angles in a range of 91-140, 91-120, or 91-100 degrees.

In a related embodiment, as shown in FIG. 2A, tabs 258 connected to respective ones of the first opposing side edge portion 138 and second opposing side edge portion 142 of the shelf panel 118 may aid in limiting travel of the support panels 122, 226 beyond the outside limit of the predetermined obtuse angle range (e.g., 140, 120, or 100 degrees). In this regard, the tabs 258 may provide support against a corresponding one of the first support panel 122 or the second support panel 226 in the case that the surface 123 of the first support panel 122 or the surface 227 of the second support panel 226 is adjacent to the tab 258. The support provided by the tab 258 can be additional support to that provided by one or more stabilizers 262 as discussed below.

In a related embodiment, the one or more stabilizers 262 may comprise cables 263a 263b. For instance, a cable 263a 263b may extend between an anchor location 266a and a given one of the first support panel 122 and the second support panel 226. In an embodiment not shown, an anchor location of a cable can be adjacent to the second opposing side edge portion 142 of the shelf panel 118. An opposite end 261a of the cable 263a may terminate on the first support panel 122. A second cable 263b may have an anchor location 266b adjacent to the first opposing side edge portion 138 of the shelf panel 118. An opposite end 261b of the cable 266b may terminate on the second support panel 226. As illustrated in FIGS. 2A-2D, the anchor location 266a for the cable 263b corresponding to the first support panel 122 may alternatively be disposed on the second support panel 226 adjacent to the cantilevered edge 130 and may terminate on the first support panel 122 adjacent to the arcuate edge 134. The second support cable 263b corresponding to the second support panel 226 may be anchored to the first support panel 122 adjacent to the cantilevered edge 130 and may terminate on the second support panel 226 adjacent to the arcuate edge 134. The termination location 261a and 261b of the cables 263a and 263b on the corresponding first support panel 122 and second support panel 226 may be disposed at an end 252 of the support panel 122 opposite that of the hinged edge portion 150.

Figure 2F:
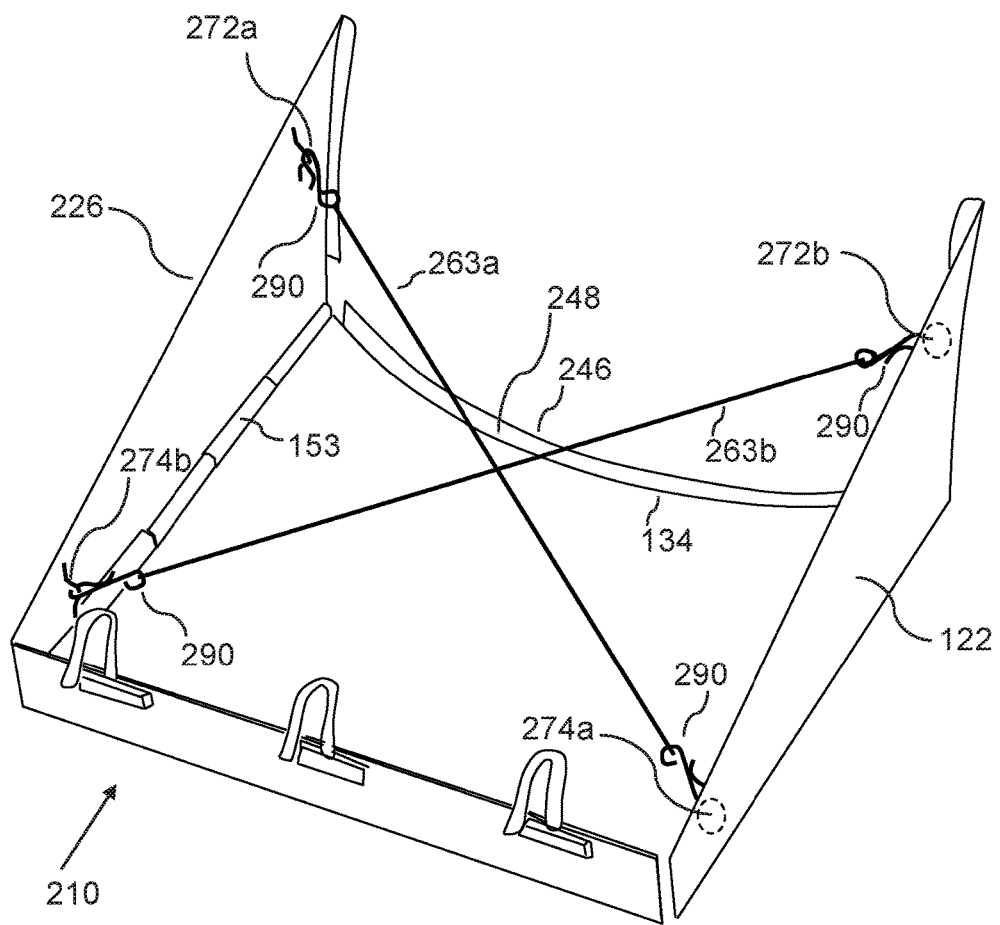
FIG. 2F is a bottom perspective view of a collapsible shelf assembly in a deployed position, according to an embodiment of the invention.

In an embodiment, as shown in FIGS. 2B and 2F, a collapsible shelf assembly 110 210 can include:
  a) a first stabilizer member 263a, which can be a cable/wire 263a; and
  b) a second stabilizer member 263b, which can be a cable/wire 263b;
  wherein the first stabilizer member 263a is connected between:
    i. an inner side connection point 272a of an inner end of the second support panel 226; and
    ii. an inner side connection point 274a of an outer end of the first support panel 122 (connection point 274a is indicated in dotted lines as seen through the first support panel 122, positioned on inner side of the first support panel 122); and
  wherein the second stabilizer member 263b is connected between:
    i. an inner side connection point 272b of an inner end of the first support panel 122 (connection point 272b is indicated in dotted lines as seen through the first support panel 122, positioned on inner side of the first support panel 122); and
    ii. an inner side connection point 274b of an outer end of the second support panel 226;
  such that the first and second stabilizer members 263a 263b are configured to cross, and thereby stabilize and strengthen the collapsible shelf assembly 110 210.

As shown in in FIG. 2F, the first and second stabilizer members 263a 263b can be configured with clip connectors 290 in first and second ends, which clip onto connection points 272a 274a 272b 274b of the first and second support panel 122 226. The collapsible shelf assembly 210, as shown, can include a single attachment member 246, with a curved/arcuate channel portion 248 that extends along substantially all of the arcuate edge 134.

Figure 4:
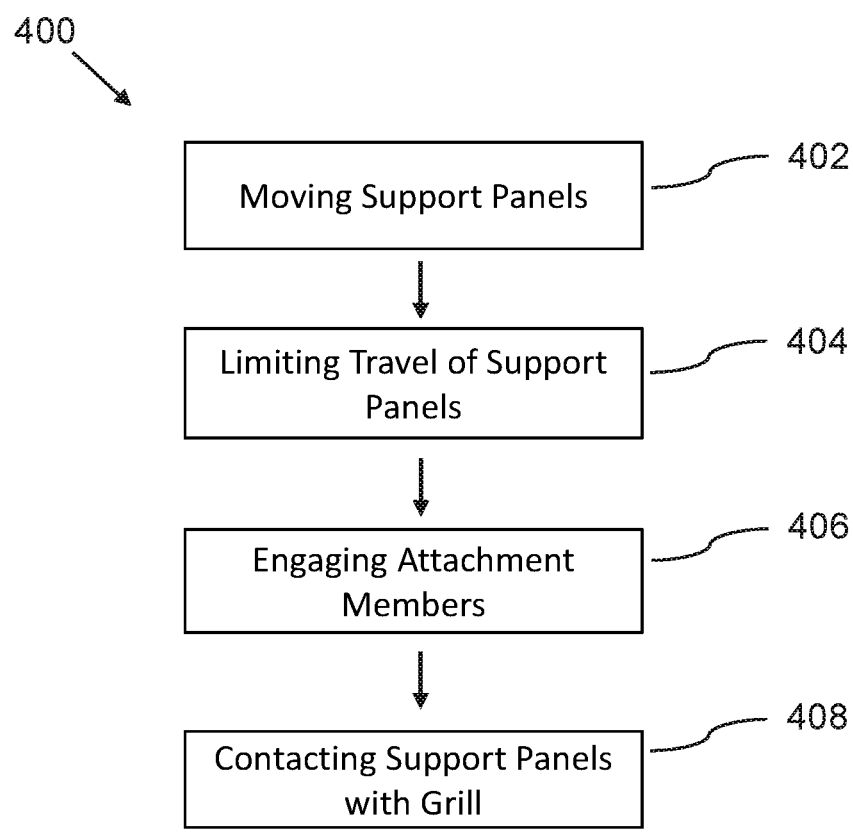
FIG. 4 is a flowchart illustrating steps that may be followed, in accordance with one embodiment of a method or process of using a collapsible shelf assembly with a grill.

In this regard, as shown in FIG. 4, a method 400 of supportably engaging a collapsible shelf assembly 110 with a grill bowl 107 may include: moving 402 the first support panel 122 and the second support panel 226 from a stowed position to a deployed position.

In a further related embodiment, the method may further include engaging 406 an attachment member 146 with an edge 109 of a grill bowl 107.

In another further related embodiment, the method 400 may further include contacting a grill bowl engagement portion 154 with a portion of the grill bowl 107. With the attachment member 146 and the grill bowl engagement portion 154 supportably engaged by the grill bowl 107, the cable 263a and cable 263b extending between the first support panel 122 and the second support panel 226 can be tensioned by way of action of the first support panel 122 and the second support panel 226 on the cable 263a and cable 263b such that travel of the support panels 122, 226 is limited to the corresponding angles 282 and 284 within the predetermined obtuse angle range discussed above.

Figure 3A:
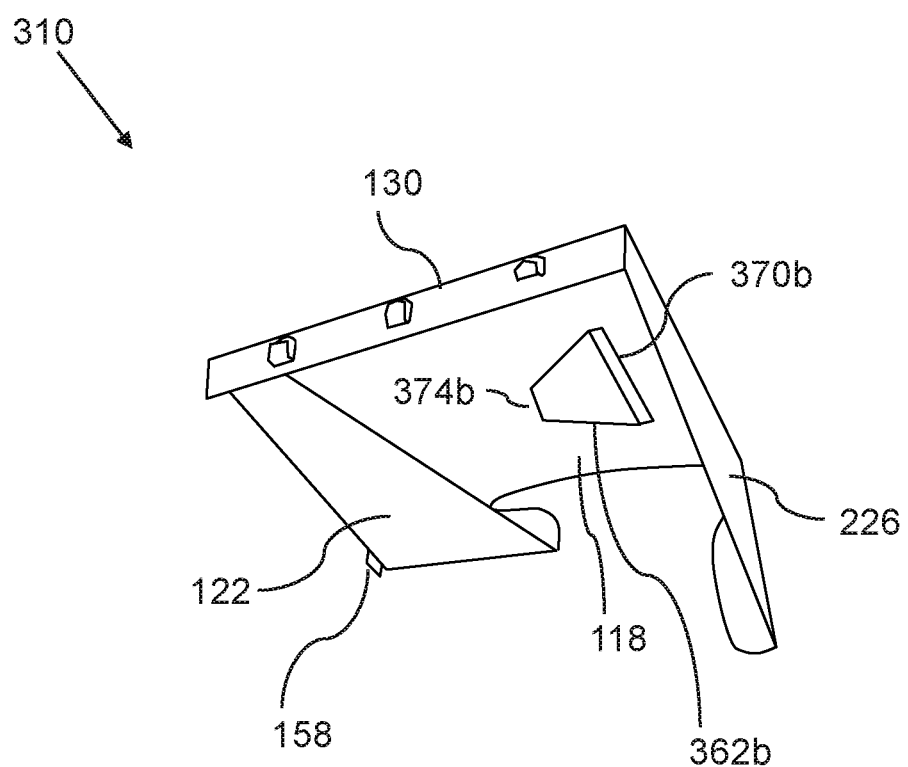
FIG. 3A is a perspective view of a collapsible shelf assembly in a partially stowed position, according to an embodiment of the invention.
Figure 3B:
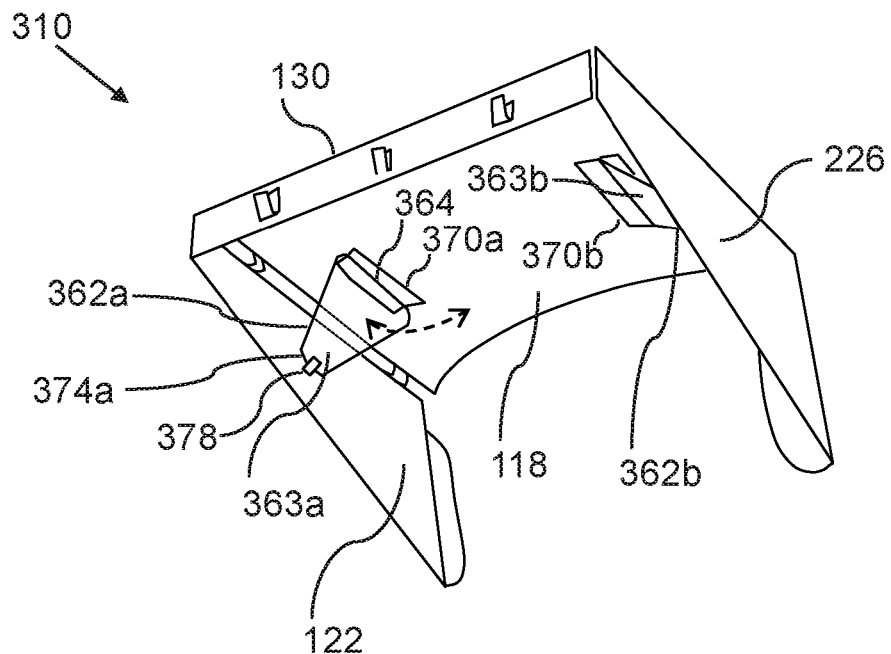
FIG. 3B is a perspective view of the collapsible shelf assembly of FIG. 2A in a deployed position, according to an embodiment of the invention.

In yet a further related embodiment, FIGS. 3A and 3B depict a collapsible shelf assembly 310, which generally includes a shelf panel 118 and a support structure as the collapsible shelf assembly 110 described above however, the collapsible shelf assembly 110 may utilize an alternate embodiment of a stabilizer 362a, 362b. In this regard, one or more stabilizers 362a, 362b may engage with each of the first support panels 122 and the second support panel 226 to secure the support panels 122, 226 in a deployed position. As illustrated in FIG. 3B, the first stabilizer 362a may engage the first support panel 122 and a second stabilizer 362b may engage the second support 226. The first stabilizer 362a and the second stabilizer 362b may be rigid members 363a, 363b extending from the shelf panel 118 to a corresponding one of the first support panel 122 or second support panel 226. The rigid members 363a, 363b may be at least generally triangularly shaped. A base side 370a, 370b of the rigid members 363a, 363b may be attached to the shelf panel 118. The rigid members 363a, 363b may be rotatable about an axis 364 of the base side 370a, 370b such that an end 374a, 374b opposite the corresponding base side 370a, 370b may be adjacent to the shelf panel 118 in a stowed configuration and attached to a corresponding one of the first support panel 122 or second support panel 226 in the deployed position. In this regard, the ends 374a, 374b may be attached to the corresponding first support panel 122 or the second support panel 226 with an engagement member 378 (e.g., hook or clip) when secured in the deployed position.

Utilizing the rigid members 363a, 363b may lock the corresponding first support panel 122 and second support panel 226 in the deployed position. Further, the rigid members 363a, 363b may prevent lateral movement of the support panels 122, 226 such that the corresponding angles 282 and 284 of support panels 122, 226 in relation to the shelf panel 118 may be maintained at a relatively constant angle. Specifically, the angles 282 and 284 may be maintained even when an external force is applied to either the first support panel 122 or the second support panel 226 that would otherwise result in the first support panel 122 or the second support panel 226 collapsing toward the stowed position.

Figure 3C:
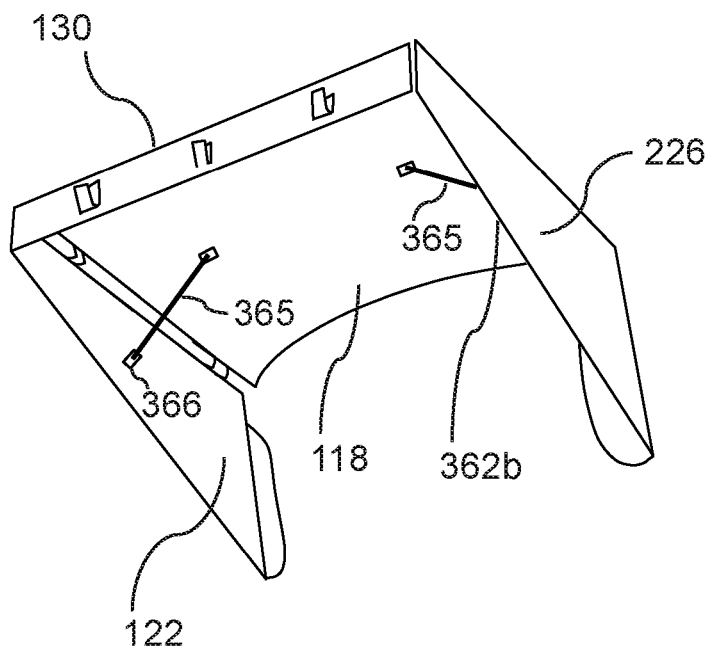
FIG. 3C is a perspective view of a collapsible shelf assembly in a deployed position, according to an embodiment of the invention.

In a further related embodiment, the stabilizer 363a, 363b may be a cable 365, as shown in FIG. 3C. When the cable 365 is in tension, i.e., in the deployed position, the cable 365 is at least generally triangularly shaped. In this alternative embodiment, two cables 365 may be connected to a corresponding first support panel 122 or second support panel 226 and the shelf panel 118 both in the deployed position and in the stowed position. Accordingly, the engagement members 366 may be a solid loop effectively preventing each of the cables 365 from being disengaged from the corresponding first support panel 122 or second support panel 226. In other words, the cable 366 may permanently be attached to both the first support panel 122 and the shelf panel 118 and the cable 365 may permanently be attached to both the second support panel 226 and the shelf panel 118.

In related embodiments, there are many benefits to utilizing the above described stabilizers 262 or 362a, 362b. When the collapsible shelf assembly 110 is loaded, the weight is disbursed between the support panels 122, 226. Without use of stabilizer 262 or 362a, 362b the support panels 122, 226 would naturally tend to move in directions opposite of each other when loaded, possibly causing the collapsible shelf assembly 110 or 310 to collapse. In this regard, the support panels 122, 226 are prevented from separating by the stabilizer 262 or 362a, 362b exerting an opposite force on the opposite support panel 226, 122, thus neutralizing the tendency of the support panels 122, 226 to move outward. Further, if a collapsible shelf assembly 110 or 310 did not include one or more stabilizer 262 or 362a, 362b and was unevenly loaded (i.e., if the weight was greater on one side of the shelf panel 118 than the other) the shelf panel 118 would tend to warp in a downward direction on that side. This tendency may be reduced and/or eliminated by utilizing one or more stabilizers 262 or 362a, 362b as described above because the uneven force on the opposing side edge portion 138, 142 of the shelf panel 118 is transferred via the one or more stabilizers 262 or 362a, 362b to the opposite side edge portion 142, 138 of the shelf panel 118.

Thus, as described in the foregoing, in an embodiment, a collapsible shelf assembly 110 adapted to be supportably engaged by a grill bowl 107, can include a) a shelf panel 118 having a surface 120 defined between a cantilevered edge portion 130 and an arcuate edge portion 134 and between opposing side edge portions 138 142, the arcuate edge portion 134 being conformingly shaped to an edge 109 of the grill bowl 107;

b) an attachment member 146 that extends along at least a portion of the arcuate edge portion 134, the attachment member 146 being adapted to engage the edge 109 of the grill bowl 107; and c) a first support panel 122 and a second support panel 226 that are each engaged with the shelf panel 118 on a portion of the shelf panel 118 opposite the surface 120 and configured to be moved between a deployed position and a stowed position;

wherein the support panels 122 226 extend in a direction away from the surface 120 when in the deployed position and the support panels 122 226 are disposed in a folded configuration substantially parallel to the surface when in the stowed position.

In a related embodiment, the collapsible shelf assembly 110 can further include:

at least one stabilizer 262 engaged with each of the first support panel 122 and the second support panel 226 to limit travel of the plurality of support panels beyond a predetermined orientation relative to the shelf panel 118 when in the deployed position.

In a further related embodiment, the at least one stabilizer 262 can be engaged with each one of the first support panel 122 and the second support panel 226 to secure the support panels in the deployed position.

In another related embodiment, the at least one stabilizer 262 can include at least one of a rigid member 363a 363b extending between:

a) a respective one of the first support panel 122 or the second support panel 226; and b) the shelf panel 118.

In yet another related embodiment, the stabilizer 262 can include a cable extending between an anchor location and a given one of the first and second support panels 122 226.

In a further related embodiment, the anchor location for the cable corresponding to the first support panel 122 can be disposed on the second support panel 226 and the anchor location for the cable corresponding to the second support panel 226 can be disposed on the first support panel 122.

In a yet further related embodiment, the anchor location for the cable corresponding to the first support panel 122 is disposed on the second support panel 226 adjacent to the cantilevered edge 130 and terminates on the first support panel 122 adjacent to the arcuate edge 134, and wherein the anchor location for the cable 365 corresponding to the second support panel 226 is disposed on the first support panel 122 adjacent to the cantilevered edge 130 and terminates on the second support panel 226 adjacent to the arcuate edge 134.

In a yet further related embodiment, when in the deployed position, the cables 263a 263b extending between the first and second support panels 122 226 can be tensioned by way of action of the first and second support panels 122 226 on the cable 263a 263b.

In a related embodiment, when in the deployed position, an included angle between the first support panel 122 and the shelf panel 118 and between the second support panel 226 and the shelf panel 118 can be obtuse.

In a further related embodiment, the first support panel 122 can extend along substantially all of a first of the opposing side edge portions 138 and the second support panel 226 can extend along substantially all of a second of the opposing side edge portions 142.

In a yet further related embodiment, the first support panel 122 can be hingedly connected to the shelf panel 118 at the first of the opposing side edge portions 138 and the second support panel 226 can be hingedly connected to the shelf panel 118 at the second of the opposing side edge portions 142.

In a related embodiment, the first support panel 122 and the second support panel 226 can each comprise a grill bowl engagement portion 154 that is contactable with a portion of the grill bowl 107 extending from the edge 109 of the grill bowl 107 when the attachment member 146 is engaged to the edge of the grill bowl 107 and the first and second support panels 122 226 are in the deployed position.

In a further related embodiment, the grill bowl engagement portion 154 can be correspondingly contoured to the portion of the grill bowl 107 extending from the edge 109 of the grill bowl.

In a yet further related embodiment, the grill bowl engagement portion 154 can include a non-slip surface 257.

In a related embodiment, the attachment member 146 can further include at least one arcuate channel portion for receiving the edge 109 of the grill bowl 107.

In a further related embodiment, the arcuate channel can extend along substantially all of the arcuate edge 134 of the shelf panel 118.

In a further related embodiment, the cantilevered edge portion 130 can include a plurality of accessory hooks 214.

In another embodiment, a collapsible shelf assembly 110 for connecting to a grill bowl 107 can include:

a shelf panel 118, comprising a front edge 134 that is configured to be conformingly shaped with an edge 109 of the grill bowl 107, such that the front edge 134 is configured to be detachably connectable to the edge 109 of the grill bowl 107;

a first support panel 122 and a second support panel 226 that are connected to respectively first and second sides of the shelf panel 118;

wherein the support panels 122 226 extend in a downward direction away from the surface 120 when in a deployed position and the support panels 122 226 are disposed in a folded configuration substantially parallel to the surface 120 when in the stowed position.

In a related embodiment, the collapsible shelf assembly 110 can further include:

at least one attachment member 146 that is connected along at least a portion of the front edge 134, such that the attachment member 146 is configured to engage with the edge 109 of the grill bowl 107.

In yet a related embodiment, the first support panel 122 and the second support panel 226 can be pivotally connected to respectively the first and the second sides of the shelf panel 118 and configured to be moved between the deployed position and a stowed position; wherein the support panels 122 226 can be disposed in a folded configuration substantially parallel to the surface when in the stowed position.

In yet a related embodiment, the attachment member can further include at least one channel portion 247, which can be curved, which channel portion 247 is configured to receive the edge of the grill bowl.

In another related embodiment, the collapsible shelf assembly 110 can further include:

at least one stabilizer 262, which is connected between the shelf panel 118 and each of the first support panel 122 and the second support panel 226, such that the at least one stabilizer 262 is configured to limit travel of the first and second support panels 122 226 beyond a predetermined orientation relative to the shelf panel 118 when in the deployed position.

In another related embodiment, the at least one stabilizer 262 can include:

a) a first stabilizer 362a member that is connected between the first support panel 122 and the shelf panel 118; and b) a second stabilizer 362b member that is connected between the second support panel 226 and the shelf panel 118.

In a further related embodiment, the first and second stabilizer members 363a 363b can be rigid members.

In another further related embodiment, the first and second stabilizer members 362a 362b can be cables.

In an embodiment, as shown in FIG. 4, a method for use of a collapsible shelf assembly with a grill bowl 400, can include:

a) moving 402 a first support panel and a second support panel from a stowed position to a deployed position, wherein the first support panel and the second support panel are each engaged with an opposite portion of a shelf panel;

b) limiting 404 the travel of the first support panel and the second support panel from the stowed position to the deployed position beyond a predetermined orientation relative to the shelf panel with at least one stabilizer engaged with each of the first support panel and the second support panel;

c) engaging 406 an attachment member, that extends along at least a portion of an arcuate edge portion of the shelf panel, with an edge of the grill bowl; and d) contacting 408 the first support panel and the second support panel with a portion of the grill extending from the edge of the grill bowl, such that the shelf panel is supportably engaged by the edge of the grill bowl and first support panel and the second support panel.

In a related embodiment of the method 400, the travel of the first support panel and the second support panel can be limited with the at least one stabilizer such that when the shelf panel is loaded, the load is distributed between the first support panel and the second support panel at least in part through the at least one stabilizer.

In another related embodiment of the method 400, the at least one stabilizer can limit the travel of the first support panel and the second support panel by tension of a cable.

In yet a related embodiment, the method 400 can further include:

engaging a first stabilizer with the first support panel and the shelf panel and a second stabilizer with the second support panel and the shelf panel, wherein the first and second stabilizers can lock the first support panel and the second support panel in the deployed position.

In yet a related embodiment, the method 400 can further include:

disengaging the attachment member from the edge of the grill bowl; and moving the first support panel and the second support panel from the deployed position to the stowed position, wherein when in the stowed position the first support panel and the second support panel are substantially parallel to the shelf panel.

Here has thus been described a multitude of embodiments of the collapsible shelf assembly 110, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Consequently, variations and modifications commensurate with the above teachings, and skill and knowledge of the relevant art, are within the scope of the present invention. For example, as shown in FIG. 2A, one or more accessory hooks 214 may be provided with the collapsible shelf assembly 110. Though the accessory hooks 214 are depicted as being disposed along the cantilevered edge 130, the accessory hooks 214 may be disposed along either of the two opposing side edge portions 138 and 142.

Many such alternative configurations are readily apparent, and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A collapsible shelf assembly adapted to be supportably engaged by a grill bowl, the collapsible shelf assembly comprising:

a shelf panel having a surface defined between a cantilevered edge portion and an arcuate edge portion and between opposing side edge portions, the arcuate edge portion being adapted to conform to an edge of the grill bowl;

an attachment member that extends along at least a portion of the arcuate edge portion, the attachment member being adapted to engage the edge of the grill bowl;

a first support panel and a second support panel that are each engaged with the shelf panel on a portion of the shelf panel opposite the surface and configured to be moved between a deployed position and a stowed position; and at least one stabilizer engaged with each of the first support panel and the second support panel to limit travel of the first and second support panels beyond a predetermined orientation relative to the shelf panel when in the deployed position;

wherein the support panels extend in a direction away from the surface when in the deployed position and the support panels are disposed in a folded configuration substantially parallel to the surface when in the stowed position.

2. The collapsible shelf assembly of claim 1, wherein the at least one stabilizer is engaged with each one of the first support panel and the second support panel to secure the support panels in the deployed position.

3. The collapsible shelf assembly of claim 2, wherein the at least one stabilizer comprises at least one of a rigid member extending between:
   a) a respective one of the first support panel or the second support panel; and
   b) the shelf panel.

4. The collapsible shelf assembly of claim 1, wherein the at least one stabilizer comprises a cable extending between an anchor location and a given one of the first and second support panels.

5. The collapsible shelf assembly of claim 4, wherein the anchor location for the cable corresponding to the first support panel is disposed on the second support panel and the anchor location for the cable corresponding to the second support panel is disposed on the first support panel.

6. The collapsible shelf assembly of claim 5, wherein the anchor location for the cable corresponding to the first support panel is disposed on the second support panel adjacent to the cantilevered edge and terminates on the first support panel adjacent to the arcuate edge, and wherein the anchor location for the cable corresponding to the second support panel is disposed on the first support panel adjacent to the cantilevered edge and terminates on the second support panel adjacent to the arcuate edge.

7. The collapsible shelf assembly of claim 6, wherein, when in the deployed position, the cables extending between the first and second support panels are tensioned by way of action of the first and second support panels on the cable.

8. The collapsible shelf assembly of claim 1, wherein, when in the deployed position, an included angle between the first support panel and the shelf panel and between the second support panel and the shelf panel is obtuse.

9. The collapsible shelf assembly of claim 8, wherein the first support panel extends along substantially all of a first of the opposing side edge portions and the second support panel extends along substantially all of a second of the opposing side edge portions.

10. The collapsible shelf assembly of claim 9, wherein the first support panel is hingedly connected to the shelf panel at the first of the opposing side edge portions and the second support panel is hingedly connected to the shelf panel at the second of the opposing side edge portions.

11. The collapsible shelf assembly of claim 1, wherein the first support panel and the second support panel each comprise a grill bowl engagement portion that is contactable with a portion of the grill bowl extending from the edge of the grill bowl when the attachment member is engaged to the edge of the grill bowl and the first and second support panels are in the deployed position.

12. The collapsible shelf assembly of claim 11, wherein the grill bowl engagement portion is correspondingly contoured to the portion of the grill bowl extending from the edge of the grill bowl.

13. The collapsible shelf assembly of claim 12, wherein the grill bowl engagement portion comprises a non-slip surface.

14. The collapsible shelf assembly of claim 1, wherein the attachment member further comprises at least one arcuate channel portion for receiving the edge of the grill bowl.

15. The collapsible shelf assembly of claim 14, wherein the arcuate channel extends along substantially all of the arcuate edge of the shelf panel.

16. The collapsible shelf assembly of claim 1, wherein the cantilevered edge portion comprises a plurality of accessory hooks.

17. The collapsible shelf assembly of claim 1, further comprising:
   a) a first stabilizer member; and
   b) a second stabilizer member;
   wherein the first stabilizer member is connected between:
      an inner side connection point of an inner end of the second support panel; and
      an inner side connection point of an outer end of the first support panel; and
   wherein the second stabilizer member is connected between:
      an inner side connection point of an inner end of the first support panel; and
      an inner side connection point of an outer end of the second support panel;
   such that the first and second stabilizer members are configured to cross, and
   thereby stabilize and strengthen the collapsible shelf assembly.

18. A collapsible shelf assembly for connecting to a grill bowl, the collapsible shelf assembly comprising:
   a shelf panel, comprising a front edge that is adapted to conform with an edge of the grill bowl, such that the front edge is configured to be detachably connectable to the edge of the grill bowl;
   a first support panel and a second support panel that are connected to respectively first and second sides of the shelf panel;
   wherein the support panels extend in a downward direction away from the surface when in a deployed position; and
   wherein, when in the deployed position, an included angle between the first support panel and the shelf panel and between the second support panel and the shelf panel is obtuse.

19. The collapsible shelf assembly of claim 18, further comprising:
   at least one attachment member that is connected along at least a portion of the front edge, such that the attachment member is configured to engage with the edge of the grill bowl.

20. The collapsible shelf assembly of claim 19, wherein the at least one attachment member further comprises at least one channel portion, which is configured to receive the edge of the grill bowl.

21. The collapsible shelf assembly of claim 18, wherein the first support panel and the second support panel are pivotally connected to respectively the first and the second sides of the shelf panel and configured to be moved between the deployed position and a stowed position; and wherein the support panels are disposed in a folded configuration substantially parallel to the surface when in the stowed position.

22. The collapsible shelf assembly of claim 18, further comprising:
at least one stabilizer, which is connected between the shelf panel and each of the first support panel and the second support panel, such that the at least one stabilizer is configured to limit travel of the first and second support panels beyond a predetermined orientation relative to the shelf panel when in the deployed position.

23. The collapsible shelf assembly of claim 22, wherein the at least one stabilizer comprises:
a first stabilizer member that is connected between the first support panel and the shelf panel; and
a second stabilizer member that is connected between the second support panel and the shelf panel.

24. The collapsible shelf assembly of claim 23, wherein the first and second stabilizer members are rigid members.

25. The collapsible shelf assembly of claim 18, further comprising:
a) a first stabilizer member; and
b) a second stabilizer member;
wherein the first stabilizer member is connected between:
an inner side connection point of an inner end of the second support panel; and
an inner side connection point of an outer end of the first support panel; and
wherein the second stabilizer member is connected between:
an inner side connection point of an inner end of the first support panel; and
an inner side connection point of an outer end of the second support panel;
such that the first and second stabilizer members are configured to cross, and thereby stabilize and strengthen the collapsible shelf assembly.

26. The collapsible shelf assembly of claim 25, wherein the first and second stabilizer members are cables.

27. A collapsible shelf assembly adapted to be supportably engaged by a grill bowl, the collapsible shelf assembly comprising:
a shelf panel having a surface defined between a cantilevered edge portion and an arcuate edge portion and between opposing side edge portions, the arcuate edge portion being adapted to conform to an edge of the grill bowl;
an attachment member that extends along at least a portion of the arcuate edge portion, the attachment member being adapted to engage the edge of the grill bowl;
a first support panel and a second support panel that are each engaged with the shelf panel on a portion of the shelf panel opposite the surface and configured to be moved between a deployed position and a stowed position;
wherein the support panels extend in a direction away from the surface when in the deployed position and the support panels are disposed in a folded configuration substantially parallel to the surface when in the stowed position;
wherein the first support panel and the second support panel each comprise a grill bowl engagement portion that is contactable with a portion of the grill bowl extending from the edge of the grill bowl when the attachment member is engaged to the edge of the grill bowl and the first and second support panels are in the deployed position; and
wherein the grill bowl engagement portion is correspondingly contoured to the portion of the grill bowl extending from the edge of the grill bowl.

* * * * *